(12) United States Patent
Kain et al.

(10) Patent No.: US 9,989,544 B2
(45) Date of Patent: Jun. 5, 2018

(54) SEQUENCE SCHEDULING AND SAMPLE DISTRIBUTION TECHNIQUES

(71) Applicant: Illumina, Inc., San Diego, CA (US)

(72) Inventors: Robert C. Kain, San Diego, CA (US); Alexander G. Dickinson, Laguna Beach, CA (US); Min-Jui Richard Shen, Poway, CA (US); Helmy A. Eltoukhy, Woodside, CA (US); Francisco Jose Garcia, San Diego, CA (US)

(73) Assignee: ILLUMINA, INC., San Diego, CA (US)

(*) Notice: Subject to any disclaimer, the term of this patent is extended or adjusted under 35 U.S.C. 154(b) by 193 days.

(21) Appl. No.: 14/795,285

(22) Filed: Jul. 9, 2015

(65) Prior Publication Data

US 2015/0309058 A1 Oct. 29, 2015

Related U.S. Application Data

(63) Continuation of application No. 13/668,686, filed on Nov. 5, 2012, now Pat. No. 9,116,139.

(51) Int. Cl.
*G01N 35/00* (2006.01)
*B01J 19/00* (2006.01)

(52) U.S. Cl.
CPC .......... *G01N 35/0092* (2013.01); *B01J 19/00* (2013.01); *G01N 35/00871* (2013.01)

(58) Field of Classification Search
CPC ............ G01N 35/0092; G01N 35/00871; B01J 19/00

USPC .............. 700/266; 702/19, 20, 22, 31, 32; 930/10; 506/43

See application file for complete search history.

(56) References Cited

U.S. PATENT DOCUMENTS

| | | | |
|---|---|---|---|
| 5,282,149 A * | 1/1994 | Grandone | G01N 35/00732 422/67 |
| 5,601,141 A | 2/1997 | Gordon et al. | |
| 6,172,218 B1 | 1/2001 | Brenner | |
| 6,306,597 B1 | 10/2001 | Macevicz | |
| 6,969,488 B2 | 11/2005 | Bridgham et al. | |

(Continued)

FOREIGN PATENT DOCUMENTS

| | | |
|---|---|---|
| WO | 2005065814 A1 | 7/2005 |
| WO | 2006064199 A1 | 6/2006 |

(Continued)

OTHER PUBLICATIONS

MJ Research PTC-0200 DNA Engine & PTC-0225 DNA Engine Tetrad Operations Manual Version 4.0 (1999).

(Continued)

*Primary Examiner* — Shogo Sasaki
(74) *Attorney, Agent, or Firm* — Fletcher Yoder PC

(57) ABSTRACT

A technique is disclosed for sample management for use in conjunction with sequencing devices that sequence biological samples, e.g., DNA and RNA. A sequencing device or a network of sequencing devices may be scheduled according to the characteristics of the samples in queue and the capabilities and availability of sequencing devices. Biological samples may be automatically queued and loaded via a sample distribution system. A sample distribution system may be used to reduce operator intervention.

21 Claims, 10 Drawing Sheets

(56) References Cited

U.S. PATENT DOCUMENTS

| | | |
|---|---|---|
| 7,001,792 B2 | 2/2006 | Sauer et al. |
| 7,057,026 B2 | 6/2006 | Barnes et al. |
| 7,329,860 B2 | 2/2008 | Feng et al. |
| 7,371,346 B2 * | 5/2008 | Windeyer ............... G01N 1/31 422/536 |
| 8,244,479 B2 | 8/2012 | Kain et al. |
| 8,315,817 B2 | 11/2012 | Kain et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2007/0243626 A1 * | 10/2007 | Windeyer ............... B01L 3/16 436/176 |
| 2008/0262172 A1 | 10/2008 | Zhao |
| 2009/0026082 A1 | 1/2009 | Rothberg et al. |
| 2009/0127589 A1 | 5/2009 | Rothberg et al. |
| 2009/0155793 A1 | 6/2009 | Oliphant |
| 2010/0137143 A1 | 6/2010 | Rothberg et al. |
| 2010/0137166 A1 | 6/2010 | Kain et al. |
| 2010/0138162 A1 | 6/2010 | Kain et al. |
| 2010/0282617 A1 | 11/2010 | Rothberg et al. |
| 2010/0323350 A1 | 12/2010 | Gordon et al. |
| 2011/0246084 A1 | 10/2011 | Ronaghi et al. |

FOREIGN PATENT DOCUMENTS

| | | |
|---|---|---|
| WO | 2007010251 A2 | 1/2007 |
| WO | 2011067559 A1 | 6/2011 |

OTHER PUBLICATIONS

Marra et al., High-throughput plasmid DNA purification for 3 cents per sample, Nucleic Acids Research, 1999, vol. 27, No. 24.

Margulies et al., Genome sequencing in microfabricated high-density picolitre reactors, Nature, vol. 437, Sep. 15, 2005/doi:10.1038/nature03959.

Bentley et al., Accurate whole human genome sequencing using reversible terminator chemistry, vol. 456, Nov. 6, 2008/doi:10.1038/nature07517.

Lundquist et al. "Parallel confocal detection of single molecules in real time", Opt. Lett. 33, 1026-1028 (2008).

Levene et al. "Zero-Mode Waveguides for Single-Molecule Analysis at High Concentrations", Science 299, 682-686 (2003).

Cockroft, et al. "A Single-Molecule Nanoprene Device Detects DNA Polymerase Activity with Single-Nucleotide Resolution", J. Am. Chem. Soc. 130, 818-820 (2008).

Healy, "Nanopore-based single-molecule DNA analysis", Nanomed. 2, 459-481 (2007).

Soni & Meller, "Progress toward Ultrafast DNA Sequencing Using Solid-State Nanopores", Clin. Chem. 53, 1996-2001 (2007).

Korlach et al. "Selective aluminum passivation for targeted immobilization of single DNA polymerase molecules in zero-mode waveguide nanostructures", Proc. Natl. Acad. Sci. USA 105, 1176-1181 (2008).

Bentley et al., Supplemental Information, www.nature.com, doi:10.10381 nature07517(2008).

\* cited by examiner

SEQUENCE SCHEDULING AND SAMPLE DISTRIBUTION TECHNIQUES

CROSS REFERENCE TO RELATED APPLICATION

This application is a continuation of U.S. patent application Ser. No. 13/668,686, now U.S. Pat. No. 9,116,139, entitled "Sequence Scheduling and Sample Distribution Techniques," filed Nov. 5, 2012, which is herein incorporated in its entirety by reference.

BACKGROUND

The present disclosure relates generally to the field of genetic sequencing. More particularly, the disclosure relates to improved techniques for throughput of automating sequencing of genetic materials by use of automated scheduling and/or automated sample distribution.

Genetic sequencing has become an increasingly important area of genetic research, promising future uses in diagnostic and other applications. In general, genetic sequencing consists of determining the order of nucleotides for a nucleic acid such as a fragment of RNA or DNA. Relatively short sequences are typically analyzed, and the resulting sequence information may be used in various bioinformatics methods to align fragments against a reference sequence or to logically fit fragments together so as to reliably determine the sequence of much more extensive lengths of genetic material from which the fragments were derived. Automated, computer-based examination of characteristic fragments have been developed, and have been used more recently in genome mapping, analysis of genetic variation between individuals, identification of genes and their function, and so forth. However, existing techniques are highly time-intensive, and resulting genomic information is accordingly extremely costly.

A number of alternative sequencing techniques are presently under investigation and development. These include the use of microarrays of genetic material that can be manipulated so as to permit parallel detection of the ordering of nucleotides in a multitude of fragments of genetic material. The arrays typically include many sites formed or disposed on a substrate. Additional materials, typically single nucleotides or strands of nucleotides (oligonucleotides), are introduced and permitted or encouraged to bind to the template of genetic material to be sequenced, thereby selectively marking the template in a sequence dependent manner. Sequence information may then be gathered by imaging the sites. In certain current techniques, for example, each nucleotide type is tagged with a fluorescent tag or dye that permits analysis of the nucleotide attached at a particular site to be determined by analysis of image data.

Although such techniques show promise for significantly improving throughput and reducing the cost of sequencing, further progress in the parallelization, speed and reliability of sequencing is desirable.

BRIEF DESCRIPTION

The present disclosure provides significant improvements in the field of nucleic acid sequencing, especially with regard to biological sample management methods. The techniques may be used for high throughput sequencing, and will typically be most useful in sequencing of DNA and RNA (including cDNA). However, the biological sample distribution and/or scheduling techniques may be used for any suitable type of sample analysis devices. In certain embodiments, the techniques may be used with a variety of sequencing approaches or technologies, including techniques often referred to as sequencing-by-synthesis (SBS), sequencing-by-ligation, pyrosequencing, nanopore sequencing and so forth. The present techniques have been found or are believed to provide for more highly automated or higher quality sequencing, permitting higher throughput and ultimately reduced sequence costs by providing improved scheduling and decreased downtime for sequencing devices. Further, the techniques facilitate improved sample loading or queuing.

In one embodiment, the present disclosure provides a novel approach for scheduling sequencing runs for a group or network of sequencing devices. For example, such a group or network may be located in a high throughput sequencing lab or a core sequencing facility. Sequencing devices represent large capital investments, and optimized scheduling of sequencing runs (e.g., sample processing, data collection, and/or analysis) avoids idle time on a sequencer and loss of resources. The techniques relate to a controller or processor-based device that assigns biological samples to sequencing devices based on parameters associated with the sample (e.g., type of assay to be performed, a priority designation) and parameters associated with the sequencing device (e.g., estimated availability, sequencing capabilities). The processor-based device accesses the relevant data and creates a sequencing schedule, including sample assignments to particular devices. The sequencing schedule is dynamic and changes according to the new information from newly added samples in the queue. For example, a higher priority sample may jump in the line over a lower priority sample. In particular embodiments, the sequencing schedule may include an assessment of in-progress sequencing. Certain sequencing runs may have collected sufficient data to assemble a sequence even if the sequencing run is not yet complete. In one example, such runs may be interrupted and the associated sequencing device reassigned to another biological sample to optimize use of the sequencing device. In another example, a sequencing device that is underutilized may be assigned another biological sample to be loaded into an in-progress run that is not interrupted for the new sample. Instead, the new sample is sequenced together with the in-progress sample. In a third example, the priority of a sample in a queue may be raised or lowered based on sequencing data obtained on a sequencing device in the network or group of devices. In such cases, two or more samples may be related and the results from a first sample may indicate that analysis of a second, related sample should be carried out on a more expedited basis that previously determined (or conversely on a lower priority basis than a third sample).

The present techniques also involve networked or distributed control of a plurality of sequencing devices to optimize the performance of the network as a whole. In certain embodiments, the network may be a star-type arrangement with a central controller. In other embodiments, the network may be a ring-type arrangement in which the controller resides on one or more of the networked sequencing devices. Regardless of the particular arrangement, the sequencing devices may be controlled or scheduled such that particular devices are in use at particular times with the goal of adjusting the processing load of the network. In one embodiment, the controller arbitrates between local processing and cloud-based processing of the sequencing data based on an estimated processing load for the network.

In another embodiment, the present techniques include a sample distribution system that is configured to facilitate sample loading into one or more sequencing devices. As opposed to techniques in which biological samples are loaded by hand into a device, the sample distribution system may provide automatic loading from a central sample station and under processor-based control. Further, the sample distribution system may be implemented as a plug-and-play arrangement that works with a variety of sequencing devices. In one embodiment, the sample distribution system is provided as a backplane arrangement that works in conjunction with a sequencing device rack. The sample distribution system may be integrated with the sequencing scheduling techniques as provided herein. That is, the instructions for loading the samples may be provided by the sequencing scheduling system. In other embodiments, the sample distribution system may be provided as a standalone system with a user interface to provide loading instructions.

The present disclosure provides a system for scheduling sequencing runs for a plurality of biological samples. The system includes a memory circuit including executable application instructions and a processor configured to execute the application instructions. The processor is configured to execute instructions for receiving information related to availability of the plurality of sequencing devices; receiving identification information for a plurality of biological samples, wherein the identification information comprises sequencing parameters and a priority designation; assigning each of the plurality of biological samples to respective sequencing devices based at least in part on the availability of each respective sequencing device and the sequencing parameters and the priority designation of each respective sample; and providing an indication that one of the plurality of biological samples is ready to be sequenced based on an availability of an assigned sequencing device.

The present disclosure also provides a sequencing device that includes a module configured to acquire digitized signal data from a first biological sample during a sequencing run. The sequencing device also includes at least one processor configured to: receive the digitized signal data; determine nucleotide identities of the first biological sample based on the digitized signal data; output one or more files comprising the nucleotide identities; analyze the nucleotide identities to determine if enough digitized signal data has been acquired from the first biological sample; communicate that the sequencing device is available when enough digitized signal data has been acquired from the first biological sample while the module is acquiring additional digitized signal data from the first biological sample; and receive an indication that the sequencing run will be interrupted and the sequencing reassigned to a second biological sample when the sequencing device is available.

The present disclosure also provides a sample distribution system. The sample distribution system includes a sample rack for storing a plurality of individual biological samples; a plurality of conduits configured to couple to each respective biological sample and to transfer each respective biological sample within the system; a sample inlet path in fluid communication with a sample loading port of a biological analysis device; a valve that controls fluid communication between the plurality of conduits and the sample inlet path such that only one conduit of the plurality of conduits is in communication with the sample inlet path at a given time and such that the biological sample coupled to the only one conduit is in fluid communication with the sample loading port via the sample inlet path; and a controller coupled to the valve and configured to receive instructions to load a biological sample into the biological analysis device and open a fluid communication pathway between a conduit coupled to the biological sample and the sample loading port.

The present disclosure also includes a sequencing network. The sequencing network includes a plurality of sequencing devices configured to acquire digitized signal data from a biological sample during a sequencing run and communicate information about the sequencing run. The sequencing network also includes a controller coupled to the plurality of sequencing devices, wherein the controller comprises: a memory circuit including executable application instructions stored therein; and a processor configured to execute the application instructions stored in the memory device, wherein the application instruction comprise instructions for: receiving the information related to sequencing run for each respective sequencing device; receiving identification information for a plurality of biological samples, wherein the identification information comprises sequencing parameters and a priority designation; and assigning each of the plurality of biological samples to respective sequencing devices based at least in part on the information related to sequencing run of each respective sequencing device and the sequencing parameters and the priority designation of each respective sample.

The present disclosure provides a system for scheduling sequencing runs for a plurality of biological samples. The system includes a memory circuit including executable application instructions stored therein; and a processor configured to execute the application instructions stored in the memory device, wherein the application instructions comprise instructions for: receiving information related to sequencing capability of the plurality of sequencing devices; receiving identification information for a plurality of biological samples, wherein the identification information comprises sequencing parameters and a priority designation; assigning each of the plurality of biological samples to respective sequencing devices based at least in part on the sequencing capability of each respective sequencing device and the sequencing parameters and the priority designation of each respective sample; and providing an indication that one of the plurality of biological samples is ready to be sequenced based on an a sequencing capability of an assigned sequencing device.

Embodiments of the present techniques are described herein by reference to biological samples for a sequencing device. The disclosure is not, however, limited by the advantages of the aforementioned embodiment. The present techniques may also be applied to devices capable of generating other types of high throughput biological data, such as microarray data or library screening data (e.g. from screening candidate drugs or from screening engineered protein variants).

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
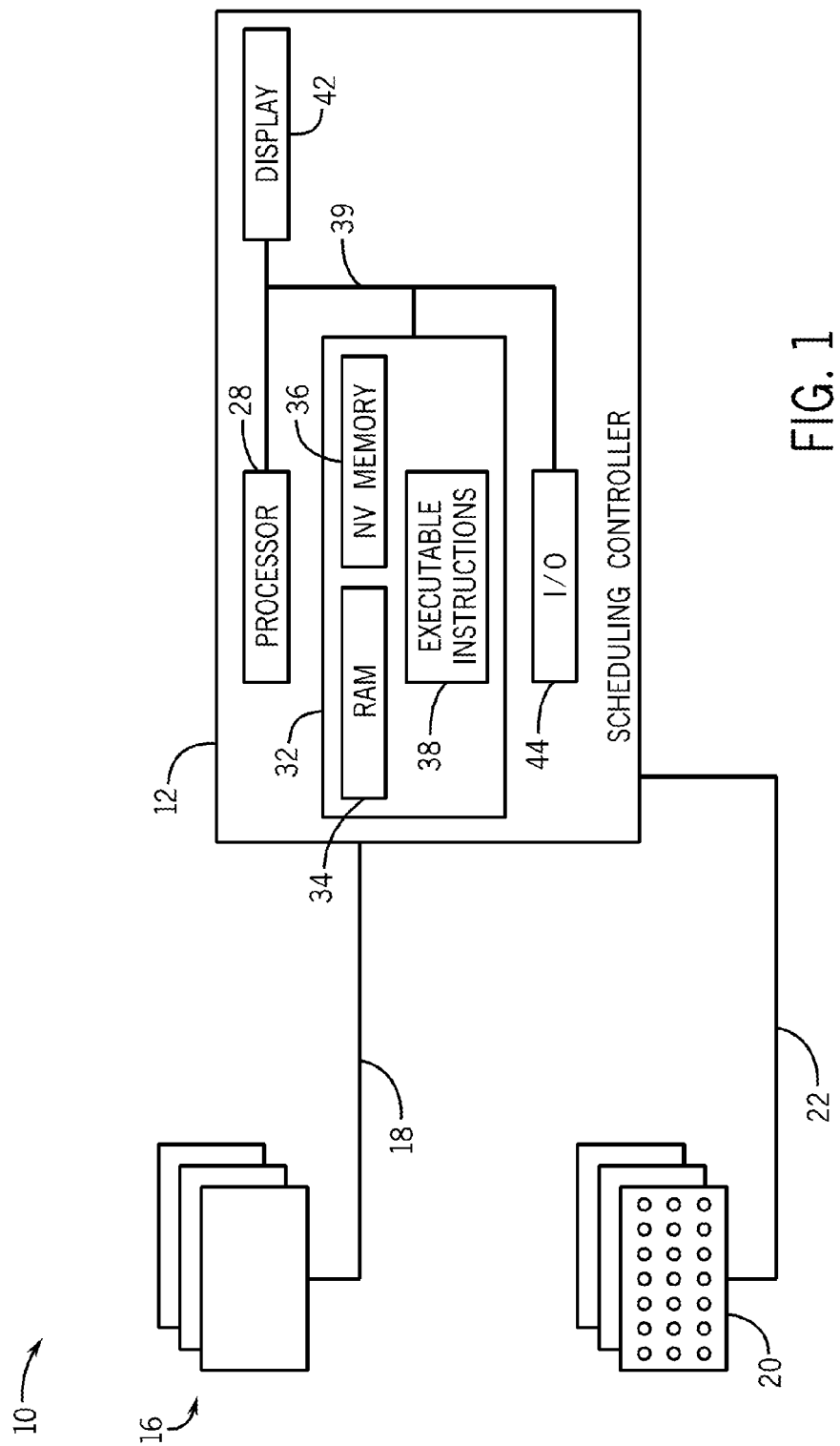
FIG. 1 is a diagrammatical overview of a sequencing system incorporating aspects of the present technique.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

Turning now to the drawings, and referring first to FIG. 1, a management system 10 for biological sample scheduling is illustrated diagrammatically. The system 10 includes one or more controllers 12 coupled to one or more sequencing devices 16 via suitable communications links 18. The system 10 also includes an input for information related to samples 20 via communication link 22. For example, each individual sample 20 may include a barcode or RFID tag that communicates with the scheduling controller 12. The communication may occur via any suitable arrangement and protocol, such as via a local area network (LAN), a general wide area network (WAN), and/or a public network (e.g., the Internet) via the communications links 18 and 24. In other embodiments, some or all of the received data may be entered by a user, including sample identification information. That is, the system 10 can be configured to receive data and information from various devices, including users of devices for generating biological data. Such data may be used to assess the availability and/or capabilities of the associated sequencing devices 16 to generate a sequencing schedule for samples that need to be analyzed. The data may also be used to generate a priority designation for the samples waiting to be analyzed. As additional samples join the queue, the system is capable of receiving additional information to create a dynamic schedule that may rearrange the proposed sequencing times if higher priority samples join the queue.

In embodiments in which there are multiple sequencing devices 16, the controller arrangement may be a star arrangement in which the sequencing devices 16 all communicate with a central controller 12. Other arrangements may include ring-based arrangement in which the controller 12 resides on or is associated with one or more sequencing devices 16. That is, the functionality of the controller 12 may be incorporated into the sequencing device 16. Further, the sequencing devices 16 may communicate with one another to distribute computing resources.

The scheduling controller 12 may be implemented as one or more of a personal computer system, server computer system, thin client, thick client, hand-held or laptop device, multiprocessor system, microprocessor-based system, set top box, programmable consumer electronic, network PC, minicomputer system, smart phone (e.g. iPhone), tablet computer (e.g. iPad), mainframe computer system, and distributed cloud computing environments that include any of the above systems or devices, and the like. The scheduling controller 12 may include one or more processors or processing units 28, a memory architecture 32 that may include RAM 34 and non-volatile memory 36. The memory architecture 32 may further include removable/non-removable, volatile/non-volatile computer system storage media. Further, the memory architecture 32 may include one or more readers for reading from and writing to a non-removable, non-volatile magnetic media, such as a hard drive, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM. The controller 12 may also include a variety of computer system readable media. Such media may be any available media that is accessible by the cloud computing environment, such as volatile and non-volatile media, and removable and non-removable media.

The memory architecture 32 may include at least one program product having a set (e.g., at least one) of program modules implemented as executable instructions that are configured to carry out the functions of the present techniques. For example, executable instructions 38 may include an operating system, one or more application programs, other program modules, and program data. Generally, program modules may include routines, programs, objects, components, logic, data structures, and so on, that perform particular tasks or implement particular abstract data types. Program modules may carry out the functions and/or methodologies of the techniques as described herein including, but not limited to, scheduling management and/or sample distribution.

The components of the controller 12 may be coupled by an internal bus 39 that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The controller may also communicate with one or more external devices such as a keyboard, a pointing device, a display 42, etc.; that enable a user to interact with the controller 12; and/or any devices (e.g., network card, modem, etc.) that enable the controller 12 to communicate with one or more other computing devices. Such communication can occur via I/O interfaces 44. Still yet, the controller 12 may communicate with one or more networks such as a local area network (LAN), a general wide area network (WAN), a public network (e.g., the Internet), and/or a cloud computing environment via a suitable network adapter.

As provided herein, the system 10 is configured to be used in conjunction with one or more devices that analyze biological samples 20. The system 10 provides a schedule for biological samples 20 to be loaded into individual devices. The system 10 may generate a proposed schedule in which waiting samples 20 are assigned an estimated sequencing time (e.g., a time to be loaded) and are assigned to a particular device. In this manner, an operator may consult the generated schedule before loading samples 20 into the sequencing devices 16. The system 10 may also generate alarms or other indications to an operator. For example, when a scheduled sample 20 is ready to be loaded into an individual sequencing device 16, the system 10 may provide an alarm or other indication to an operator. In one embodiment, the system 10 may send a text message to a pager or mobile device indicating that a sample 20 is ready to be loaded. The system 10 may also acknowledge that a particular sample 20 has been loaded and update the schedule accordingly. In one embodiment, the sample 20 is scanned before being loaded and the sample information is stored by the controller 12. In another embodiment, an operator may confirm that the sample 20 has been loaded. Although embodiments of the present disclosure are depicted in conjunction with sequencing devices, it should be understood that, in certain embodiments, the present techniques may be used in conjunction with other types of devices. Further, the present techniques may also be used in conjunction with an automatic sample distribution system. In such embodiments, the samples 20 are loaded without operator intervention.

The controller 12 may provide a user interface that guides an operator through a series of setup options. For example, upon receiving a sample 20, the operator may specify information about the sample 20 (desired assay types, priority information, sample preparation information, patient information, organism, date or time of sample collection, location of sample collection, circumstances of sample collection, suspected sample characteristics, etc.) and may select from available sequencing devices that may be appropriate. Accordingly, even though the controller 12 may be configured to match the sample 20 to the sequencing device 16 according to a rules-based protocol, the operator may also add conditions or parameters that override the protocol. For example, the sample 20 may be prepared according to a kit that is optimized for use with sequencing devices from a particular manufacturer. In such an embodiment, the operator may specify the sample 20 should be matched to sequencing devices 16 from that manufacturer. In other embodiments, the user interface may provide menu options that prompt user input with regard to particular sample preparation kits or tagging and use the information in the matching protocol.

Figure 2:
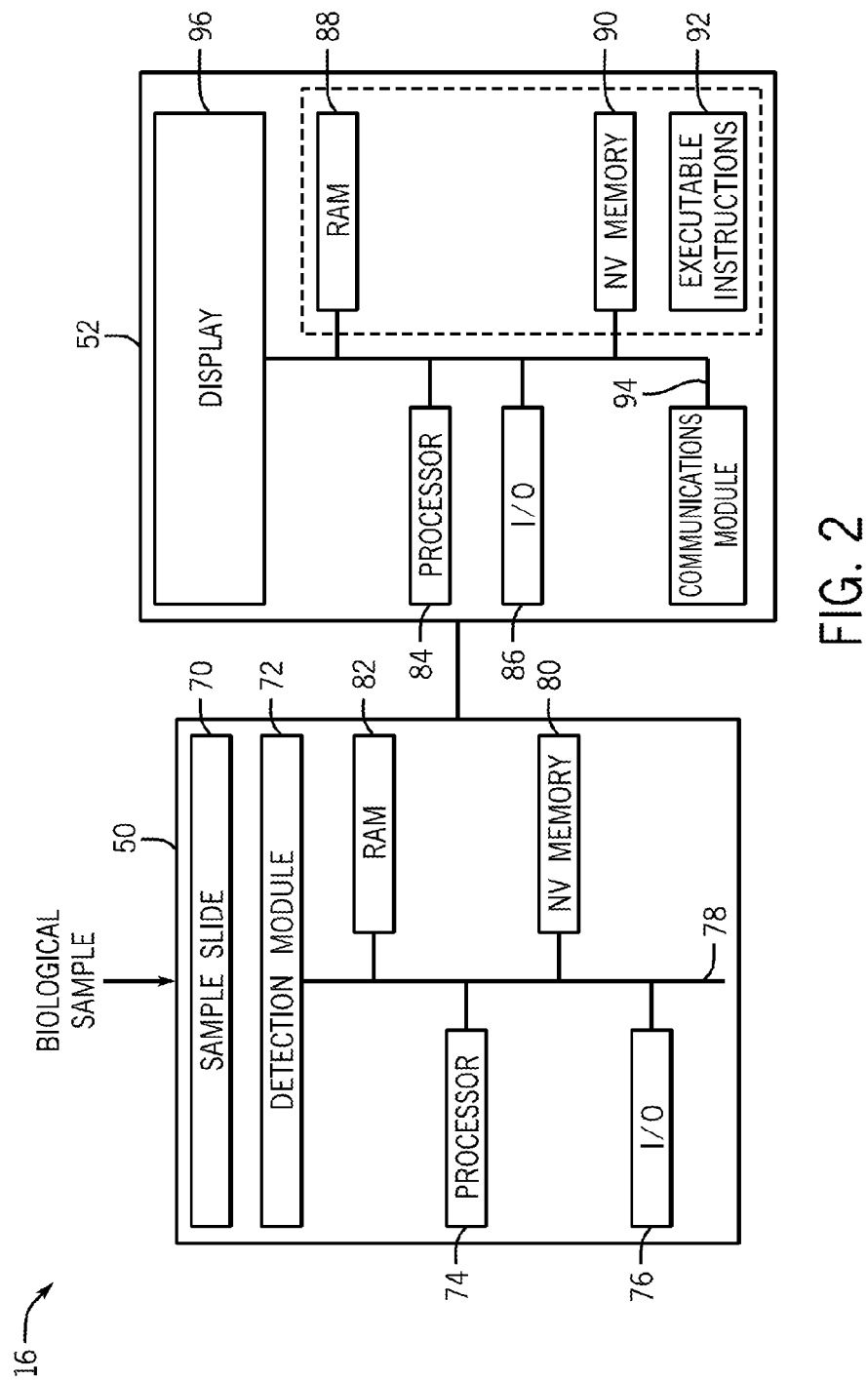
FIG. 2 is a diagrammatical overview of a sequencing device that may be used in conjunction with the system of the type discussed with reference to FIG. 1.

FIG. 2 is a schematic diagram of the sequencing device 16 that may be used in conjunction with the system 10. The sequence device 16 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 16. Such techniques use DNA ligase to incorporate oligonucleotides and identify the incorporation of such oligonucleotides and are described in U.S. Pat. No. 6,969,488; U.S. Pat. No. 6,172,218; and U.S. Pat. No. 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified, for example, by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FIS- SEQ), and Massively Parallel Signature Sequencing (MPSS). In particular embodiments, the sequencing device 16 may be a HiSeq, MiSeq, or HiScanSQ from Illumina (San Diego, Calif.).

Different types of sequencing devices can provide different advantages and disadvantages. For example, different sequencing devices vary in raw read length (e.g. length of contiguous nucleotide positions that are determined for a given nucleic acid fragment in a single instrument run), raw read accuracy (e.g. probability of an error occurring in the read of a particular nucleic acid fragment), depth of sequencing provided per run (e.g. number of nucleic acid fragments read in a run), accuracy in determining the length of homopolymeric regions, and accuracy in reading sequence regions having particular compositions (e.g. GC rich regions vs. AT rich regions). An advantage of having a variety of types of sequencing devices in a network or group of sequencing devices is that a particular device can be selected to suit a desired inquiry. For example, in an application where overall accuracy is of paramount importance it may be desirable to select a sequencer that provides a high depth of sequencing (which results in increased accuracy after data analysis) even if this means using a device that has shorter overall read length. Alternatively, for de novo genome sequencing applications it may be more desirable to select a sequencer that generates longer read lengths even if the selected device is not the most accurate in the network. Of course a particular sample can be sequenced on multiple types of sequencing devices to obtain the combined benefits of more than one device.

In accordance with the systems and methods set forth herein, particular samples can be prioritized for use on a certain type of sequencer based on sample characteristics, data quality (or quantity) expectations etc. A change can be made in this priority for a particular sample in a queue based on data obtained for a related or similar sample. For example, several related samples can be initially slated for sequencing on a first device that generates longer read lengths than a second device but that is not as accurate at determining homopolymer lengths as the second device. In the event that sequencing of one of the samples indicates the presence of homopolymer regions of interest, the priority of the related samples in the queue can be changed to shunt them to the second sequencing device where more accurate reads of homopolymer regions can be obtained. Similarly, several related samples can be initially prioritized for evaluation using a particular protocol (which, in certain embodiments, may include preset, user modified, or custom protocols), and the priority for samples in the queue for that protocol can be modified based on results obtained for one of the samples. For example, samples that were initially designated for a relatively time consuming, deep sequencing protocol can be re-designated for a lower depth and faster protocol if the results from a first sample indicate an urgent need to get preliminary data. Such a situation can arise for example, if it becomes apparent from sequencing data that the first sample contained a fast acting pathogen that should be rapidly diagnosed in the other samples. In one example, a sequencing run may determine is a sample is positive for *salmonella* DNA. The runs may proceed until identification is possible.

In one embodiment, the sample priority may be based on a desired error rate. That is, certain samples may have a wider tolerance of acceptable error rates (depending on the end use of the sequencing data), and may be scheduled on a wider array of assays and/or devices relative to a sample with more stringent or lower error rate specifications (e.g., forensic samples). For example, an estimated potential error rate may be related to the number of reads and/or the length of the reads as well as the number of cycles. In another embodiment, a run may be continued until a determination is made that an error rate is too high for adequate data analysis.

The disclosed techniques may also incorporate scheduling or assignment information for other types of analysis devices or orthogonal techniques (purification, chromatography, SNP analysis, etc, antibody or PCR-based techniques). Further, the sequencing runs may be followed by a recommended or independent validation step In the depicted embodiment, the sequencing device 16 includes a separate sample processing device 50 and an associated computer 52. However, these may be implemented as a single device. Further, the associated computer 52 may be local to or networked with the sample processing device 50. The devices may include identification components, such as barcodes or RFID tags, that facilitate identification of users, samples, and/or devices. In other embodiments, the computer 52 may be capable of communicating with a cloud computing environment that is remote from the sequencing device 16. That is, the computer 52 may be capable of communicating with the sequencing device 16 through the cloud computing environment. In the depicted embodiment, the biological sample may be loaded into the sample processing device 50 as a sample slide 70 that is detected to generate sequence data. For example, reagents that interact with the biological sample may fluoresce at particular wavelengths in response to an excitation beam generated by a detection module 72 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the detection module 72. Although the system of FIG. 2 is exemplified in regard to an optical imaging detector, it will be understood that other detectors can be used. The detection module can be physically separated from the sample slide, for example via an optical train used in many imaging devices. Alternatively, the detection module can be integrated with the slide (or other sample carrier), for example, as is the case for nanopore sequencing devices and CMOS-based proton detection devices set forth previously herein including in the incorporated references.

Taking the example of optical detection systems, the imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The detection module 72 may be under processor control, e.g., via a processor 74, and the sample receiving device 18 may also include I/O controls 76, an internal bus 78, non-volatile memory 80, RAM 82 and any other memory structure such that the memory is capable of storing executable instructions, and other suitable hardware components that may be similar to those described with regard to FIG. 2. Further, the associated computer 20 may also include a processor 84, I/O controls 86, a communications module 87, and a memory architecture including RAM 88 and non-volatile memory 90, such that the memory architecture is capable of storing executable instructions 92. The hardware components may be linked by an internal bus 94, which may also link to the display 96. In embodiments in which the sequencing device 16 is implemented as an all-in-one device, certain redundant hardware elements may be eliminated. Further, the sequencing device 16 may also interact with the cloud computing environment. Such embodiments may be beneficial for distributing processing load for the system 10.

The system 10 may include multiple sequencing devices 16, each with the same or different capabilities. That is, the sequencing devices 16 may be capable of performing different types of assays or sequencing runs, including DNA sequencing, RNA sequencing, genotyping, SNP testing, CNV analysis, methylation analysis, gene expression analysis, agrigenomics, cytogenetics, and/or cancer genomics. Further, devices with similar assay capabilities (e.g., DNA sequencing) may perform at different speeds, with different resolution, and with different sample preparation specifications. The system 10 may be capable of tracking such differences to assign the sample 20 to the appropriate sequencing device 16. In particular embodiments, the devices 16 may operate with a cartridge system that allows the devices to switch assay capabilities via the changing out of internal cartridges. Certain other components are associated with a device housing and are interoperable with a variety of cartridges. In this manner, each device 16, when available, may offer a range of assay capabilities depending on the characteristics of the inserted cartridge.

Figure 3:
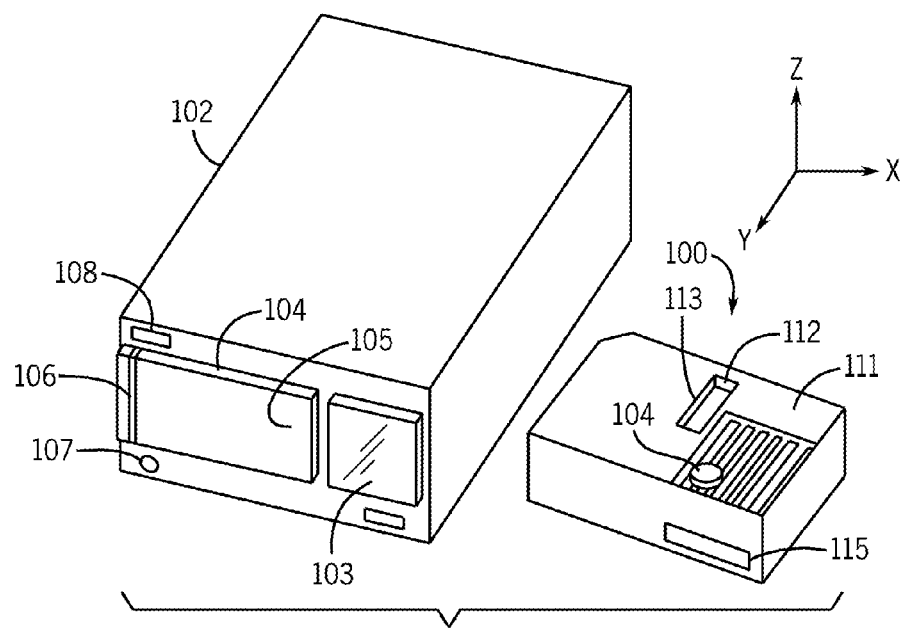
FIG. 3 is a perspective view of a sequencing device including a sample cartridge that may be used in conjunction with the system of the type discussed with reference to FIG. 1.

FIG. 3 shows an exemplary sequencing device 16 that incorporates a cartridge 100 that is configured to be inserted into a housing 102. The cartridge 100 exploits advantages of integrated optoelectronics and cartridge-based fluidics that are provided by several embodiments set forth herein. The housing 102 contains various fixed components including, for example, optical components, computational components, power source, fan and the like. A screen 103 present, for example, on the front face of the housing 102 functions as a graphical user interface that can provide various types of information such as operational status, status of an analytical procedure (e.g. a sequencing run) being carried out, status of data transfer to or from the device 16, instructions for use, warnings or the like. A cartridge receptacle 104 is also present on the front face of the housing 102. As shown, the cartridge receptacle 104 can be configured as a slot having a protective door 105. A status indicator 106, in the form of an indicator light on the frame of the cartridge receptacle in this example, is present and can be configured to indicate the presence or absence of a cartridge in the device 16. For example the indicator light 106 can change from on to off or from one color to another to indicate presence or absence of a cartridge. A power control button 107 is present on the front face of the housing 102 in this example as is identifying indicia 108 such as the name of the manufacturer or instrument. In particular embodiments, the cartridge 100 may include an identification element that communicates via handshake with the housing 102 to confirm that the cartridge is compatible with the processing elements available in the housing 102.

The cartridge 100 can be used to provide a sample and reagents to the device 16. The fluidic cartridge 100 includes a housing 111 that protects various fluidic components such as reservoirs, fluidic connections, pumps, valves and the like. A flow cell 112 is integrated into the fluidic cartridge in a position where it is in fluid communication with reagents within the housing. The housing 111 has an opening 113 through which a face of the flow cell 112 is exposed such that it can interact optically with the optical scanning device when the fluidic cartridge 100 is placed in the cartridge receptacle 104. The cartridge housing 111 also includes a sample port 114 for introduction of a target nucleic acid sample. A bar code 115 or other machine readable indicia can optionally be present on the cartridge housing 111, for example, to provide assay capability tracking and management. Other indicia 116 can also be present on the housing for convenient identification by a human user, for example, to identify the manufacturer, analytical analysis supported by the fluidic cartridge, lot number, expiration date, safety warnings and the like. The apparatus shown in FIG. 3 is exemplary.

In some embodiments, the cartridge 100 may include additional features, such as the light source (e.g., LEDs) that are configured to provide excitation light to the reactions sites of the biosensor. The cartridge 100 may also include a fluidic storage system (e.g., storage for reagents, sample, and buffer) and a fluidic control system (e.g., pumps, valves, and the like) for fluidically transporting reaction components, sample, and the like to the reaction sites. For example, after the biosensor component of the cartridge is prepared or manufactured, the biosensor may be coupled to a housing or container of the cartridge. In some embodiments, the cartridges 100 may be self-contained, disposable units. However, other embodiments may include an assembly with removable parts that allow a user to access an interior of the cartridge 100 for maintenance or replacement of components or samples. The cartridge 100 may be removably coupled or engaged to larger bioassay systems, such as a sequencing system, that conducts controlled reactions therein.

Figure 4:
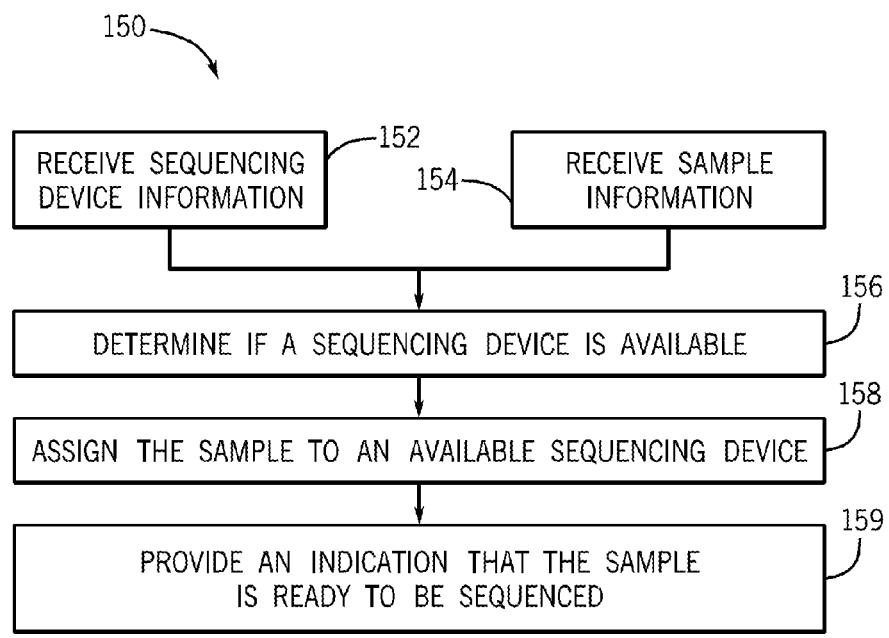
FIG. 4 is a flow diagram of a method of interaction between a sequencing device and a scheduling controller that may be performed in conjunction with the system discussed with reference to FIG. 1.

FIG. 4 is a process flow diagram illustrating a method of sequencing schedule management in accordance with some embodiments. The method is generally indicated by reference number 150 and includes various steps or actions represented by blocks. It should be noted that the method 150 may be performed as an automated procedure by a system, such as system 10. Further, certain steps or portions of the method may be performed by a single device (e.g., a controller 12) or by separate devices (e.g. a controller 12 and a sequencing device 16). In embodiments, the method 150 may be performed periodically as new information or samples enter the system 10 or as samples exit the system 10.

According to the exemplary embodiment illustrated, the method 150 begins with the steps of receiving sequencing device information at block 152 and receiving sample information at block 154. The sequencing device information may include one or more of: identification information (e.g., manufacturer, model number) for a sequencing device 16, assay capability information, information about samples that have been loaded into a particular sequencing device 16, estimated availability of a sequencing device 16, and sequencing data. In certain embodiments, certain information about the sequencing devices 16 (e.g., assay capability information) may be stored on the controller 12 and looked up in response to receiving identification information from a particular device 16. For sequencing devices 16 that incorporate a cartridge 100, block 152 may also include information about the assay capabilities of any inserted cartridge 100. The sample information may include identification information (e.g., patient information), sample type, preparation information, desired assay types, and a priority designation (e.g., high priority, default or medium priority, low priority). The method 150 assigns the sample to a sequencing device 16 based on a best match between the sequencing device information and the sample information at block 158.

The controller 12 may use any appropriate algorithm or technique for matching a sample to a sequencing device 16 based on the available criteria. Such algorithms may implement Bayesian optimization algorithms, heuristic approaches, colony optimization algorithms, genetic algorithms, Monte Carlo modeling, and/or weighted approaches. Matching solutions may be optimized with a goal that any particular sequencing device 16 is operating on a continuous flow basis. Other constraints may include null solutions when the assay capabilities of a sequencing device 16 do not match the desired assays for the sample.

At block 159, the method 150 provides an indication that the sample is ready to be sequenced and/or is assigned to a particular sequencing device 16. The indication may be in the form of a generated schedule that may be viewed by an operator. Further, the indication may be a text-based indication or an alarm. In other embodiments, the indication may be an output sent to an automatic sample loading system.

Figure 5:
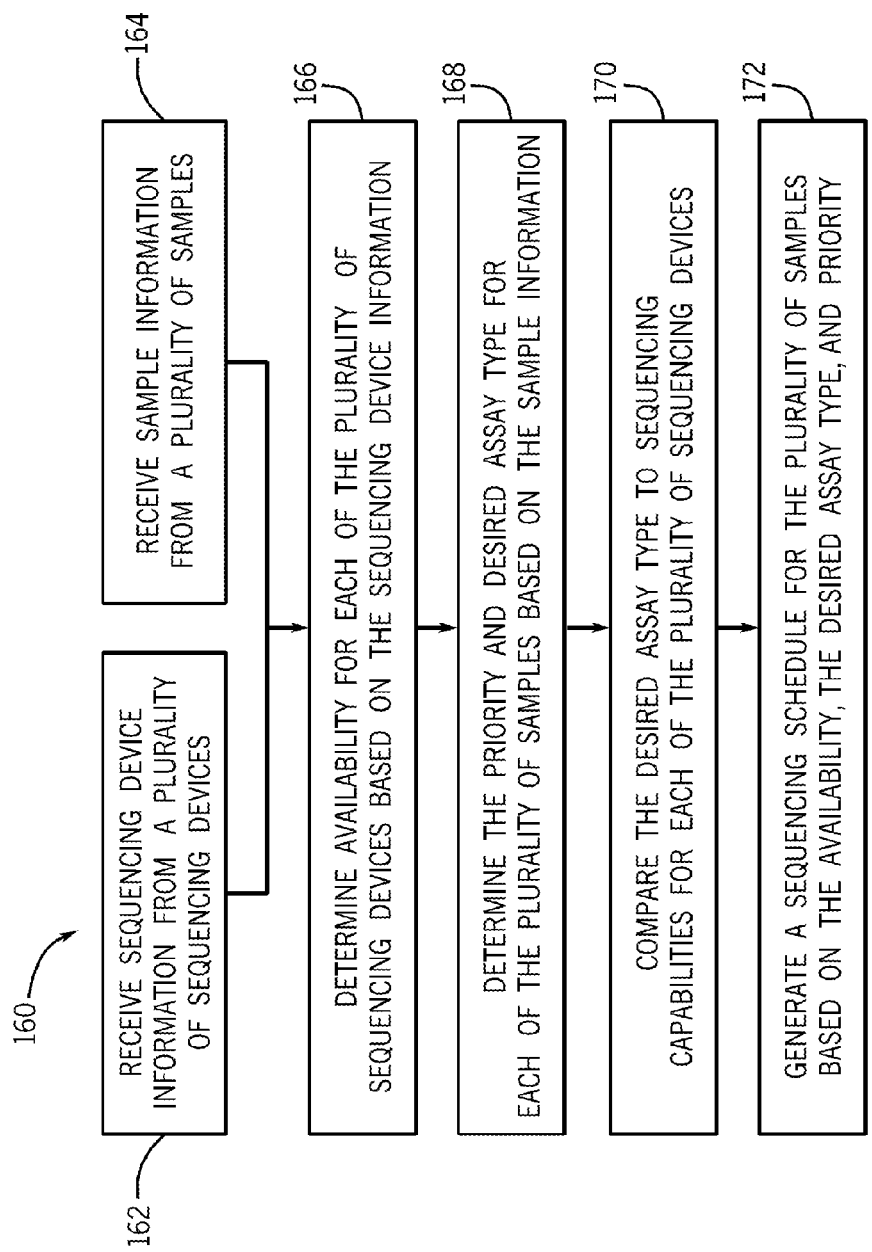
FIG. 5 is a flow diagram of a method of interaction between a plurality of sequencing devices and a scheduling controller that may be performed in conjunction with the system discussed with reference to FIG. 1.

The techniques may also be applied to more complex systems that include multiple sequencing devices and multiples samples. FIG. 5 is a flow diagram of a method 160 that includes the steps of receiving sequencing device information from a plurality of sequencing devices at block 162 and receiving sample information from a plurality of samples at block 164. The method 160 determines the availability of each sequencing device at block 166. The availability may be based on a signal from a particular sequencing device 16 or, in particular embodiments a lack of a signal. That is, an unavailable sequencing device 16 may send a signal while a sequencing run is in progress. The lack of any such signal may be an indication that the device 16 is available. In other embodiments, the sequencing device may send an estimated availability time based on an estimated time of completion of an ongoing sequencing run. The method 160 also determines a sequencing schedule based on sample information, such as a desired assay type, at block 168. At block 170, the method 160 compares the desired assay type for each sample to the sequencing capabilities of the sequencing devices 16. Finally, the method 160 generates a sequencing schedule for the samples based on the availability, the desired assay type, and any priority designation for the samples based on the scheduling instructions, including weighting for particular factors, at block 172.

Figure 6:
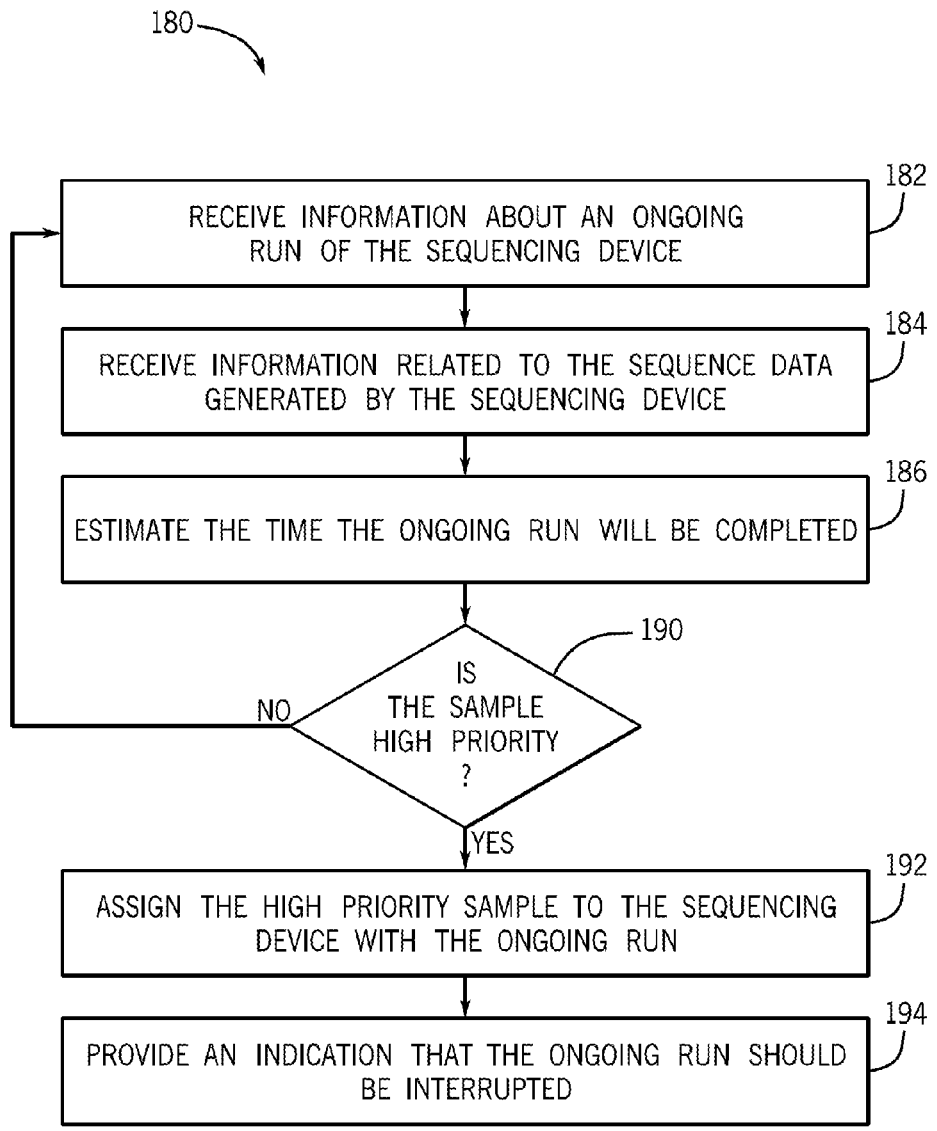
FIG. 6 is a flow diagram of a method of generating a sequencing sample schedule that may be performed in conjunction with the system discussed with reference to FIG. 1.

In a particular embodiment, the system 10 may provide override instructions for a case in which no sequencing devices 16 are available for a high priority sample, as illustrated in FIG. 6. The method 180 begins with the system 10 receiving information about an ongoing run from an unavailable sequencing device at block 182. The method 180 further receives information about the sequencing data generated by the sequencing device 16 at block 184 and an estimated time of completion at block 186. In one embodiment, the sequencing device 16 generates nucleotide identity files on a rolling basis as the run progresses. Genome assembly based on the nucleotide identity files may be completed even before the sequencing run is complete if sufficient information has been collected. That is, genome sequencing may generate a certain percentage of redundant sequencing data. However, a genome may be assembled from an incomplete set of nucleotide identity files if sufficient data has been collected. In particular embodiments, the sequencing device 16 may perform the assessment of whether sufficient data has been collected for the assay in question. In other embodiments, the nucleotide identity files may be sent to the controller 12, and the controller 12 may perform the assessment. The assessment may be based on an attempt to assemble at least a portion of the genome from a minimum file set. In other embodiments, the assessment may be based on empirical observation of a minimum run time or percentage completion of a run to achieve a sufficient data set. For example, the system 10 may include a look up table of a percentage of minimum completion for types of organisms and particular assays. In such a case, i.e., if sufficient data has been collected to achieve a desired assay result, if the sample is high priority (block 190), the sample may be assigned to the sequencing device 16 that is in use (e.g., theoretically not available) at block 192 and the method 180 provides an indication that the ongoing run should be interrupted at block 194 so that the higher priority sample can be loaded into the device 16. Otherwise, for lower priority samples in the queue, even if the collected data set is sufficient or represents a minimum required set, the sequencing run is permitted to run to completion and the method 180 returns to block 182. That is, sequencing runs may be interrupted only for high priority samples and, in particular embodiments, only if sufficient data has been collected from the run.

Figure 7:
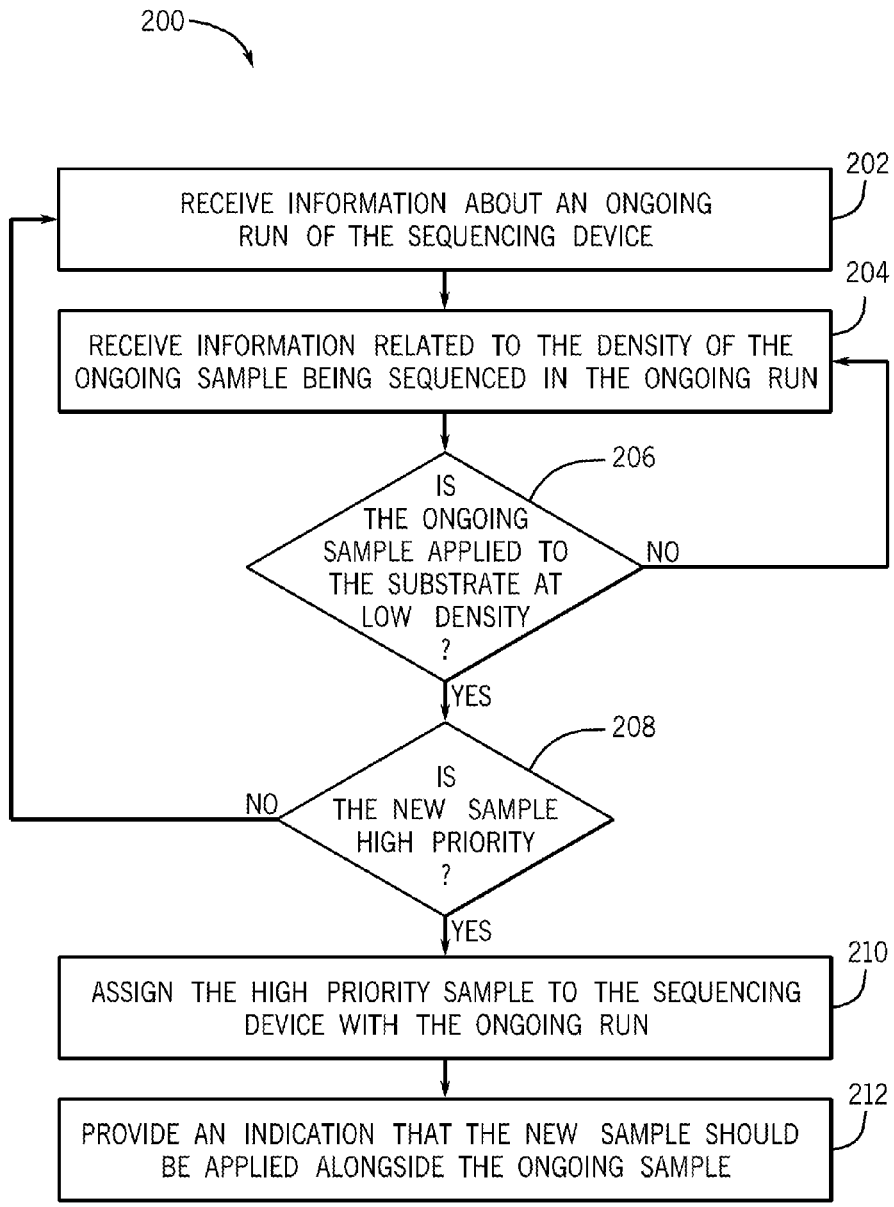
FIG. 7 is a flow diagram of a method of generating a sequencing sample schedule that may be performed in conjunction with the system discussed with reference to FIG. 1.

In another embodiment, the override instructions may provide instructions to load a high priority sample alongside the sample of an ongoing run, as illustrated in FIG. 7. The method 200 beings with the system 10 receiving information about an ongoing run from an unavailable sequencing device at block 202. The method 200 further receives information about a sample density of the sample being sequenced at block 204. If the ongoing samples is applied at low density (block 206), the device may be available for high priority samples (block 208). If both conditions are true, the sample is assigned to the device 16 at block 210 and an indication is provided that the sample should be applied alongside the sample being sequenced. Depending on the characteristics of the ongoing sample and the high priority sample, the high priority sample may be tagged to distinguish the sample from the ongoing run. Further, the samples may be related (e.g., from the same organism or individual) or unrelated (e.g., different organisms or individuals). For example tagging may occur via the Multiplexing Sample Preparation Oligonucleotide Kit (Illumina) Such an embodiment may take advantage of a sequencing run that is plated at low density, which may occur if a control library is being sequenced or for low diversity samples (e.g., expression studies with an overrepresentation of one type of transcript, amplicon pools, adapter dimer, and initial cycle indexing). In one embodiment, a high throughput lab may keep one device 16 with samples plated at low density at all times to serve as an overflow machine for incoming high priority samples.

In another embodiment, the system 10 may schedule runs of a certain type together. For example, for a scheduled whole genome or a whole chromosome sequencing run, a device 16 may hold the run until enough samples are loaded. In one embodiment, the samples may represent different individuals.

Figure 8:
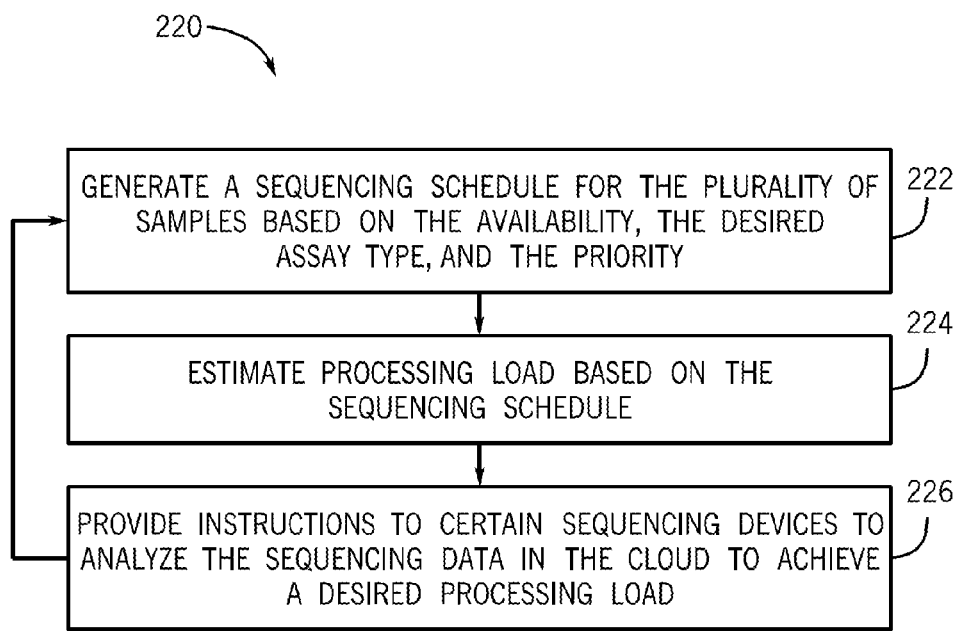
FIG. 8 is a flow diagram of a method of distributing sample analysis that may be performed in conjunction with the system discussed with reference to FIG. 1.

Other scheduling considerations for the controller 12 may include load balancing. FIG. 8 is a flow diagram of a method 220 for shifting processing loads based on a total processing burden of the system 10. After a sequencing schedule has been generated according to the techniques described herein (block 222), a total processing load may be estimated that follows the sequencing schedule (block 224). The processing load per sequencing device 16 may be estimated based on a variety of factors, including manufacturer specifications, sample type, assay type, duration of sequencing run, and/or density of plating. The processing load of the entire system 10 is based on the combined processing load of the individual sequencing devices 16 within the system 10 and may vary as the use of each sequencing device 16 changes over time according to the generated sequencing schedule. Because high processing loads may be costly, it may be advantageous to distribute the processing load between local sequencing devices 16 and a cloud computing environment if the processing load exceeds a certain threshold. In one embodiment, the system 10 provides instructions to sequencing devices 16 that are in communication with the cloud to perform data analysis in the cloud (block 226), thus reducing the local processing load. Such instructions may be provided automatically upon generation of the sequencing schedule and a determination that the estimated processing load exceeds a desirable threshold for a particular time period.

In particular embodiments, the processing load, including any availability of cloud-based processing resources, may be a factor used in determining the sequencing schedule. For example, the sequencing schedule may be optimized to smooth the processing load over time. In other embodiment, the sequencing schedule may be optimized to shift higher processing loads to times when processing power may be cheaper (e.g., at night).

Figure 9:
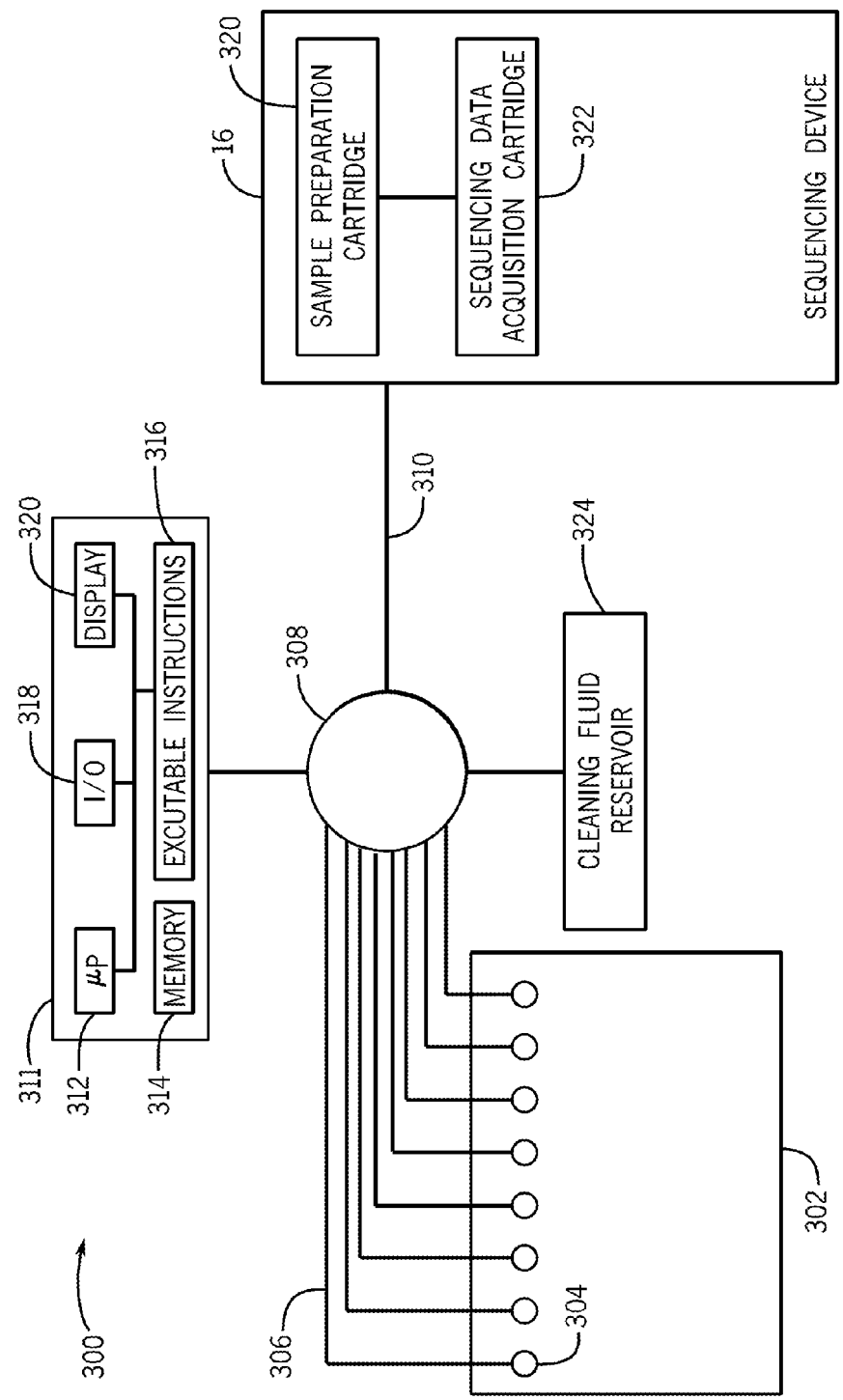
FIG. 9 is a diagrammatical overview of a sample distribution system incorporating aspects of the present technique.

As described herein, the system 10 generates a sequencing schedule to accommodate a queue of biological samples. The sequencing schedule reduces operator decision making and optimizes efficient use of resources. In particular embodiments of the disclosure, one or more sequencing devices 16 may also be used in conjunction with an automatic sample distribution system 300, as illustrated diagrammatically in FIG. 9. The sample distribution system 300 may be used either as a standalone system or in conjunction with the sequence scheduling system 10. Further, while certain embodiments may depict sample loading implementations, the disclosed techniques may also be used to load samples and/or assay cartridges. That is, the loading may be implemented on a per-cartridge basis. The sample distribution system 300 includes a sample holder or rack 302 with individual sample slots 304. Each sample slot 304 is in fluid communication with respective conduits 306. As used herein, the term "fluid communication" or "fluidically coupled" refers to two spatial regions being connected together such that a liquid or gas may flow between the two spatial regions. The terms "in fluid communication" or "fluidically coupled" allow for two spatial regions being in fluid communication through one or more valves, restrictors, or other fluidic components that are configured to control or regulate a flow of fluid through the system 300. The system 300 may include one or more pumps or pneumatic devices to pull fluid through the system in the direction of the sequencing device 16.

The respective conduits 306 are coupled to a fluid junction 308 that includes a valve or other one-way control. The fluid junction 308 allows the fluid from only one of the conduits 306 to enter an inlet path 310 at a particular time. The inlet path 310 is in fluid communication with a sample loading port of the sequencing device 16. Accordingly, when the fluid junction 308 is coupled to a specific conduit 306, the sample from a single sample slot 304 is allowed to enter the inlet path 310. The fluid junction 308 may be coupled to a sample controller 311, which includes a processor 312, a memory architecture 314 storing executable instructions 316. In specific embodiments, the sample controller 311 may include operator input/output controls 318 and a display 320. Accordingly, an operator may specify that a sample is ready to be loaded into the sequencing device and provide instructions to the fluid junction 308 via the sample controller 311 to allow the sample to enter the inlet path 310 and the sequencing device 16. In one example, the sample controller 311 may be implemented together with the scheduling controller 12 (see FIG. 1) to provide automatic distribution of scheduled samples to assigned devices.

In one embodiment of the present techniques, multiple samples may be queued in the inlet path 310. For example, the fluid junction may permit entry of the sample from one conduit 306, then close that pathway and allow entry of a second sample. The pathway may be cleaned between samples via a cleaning fluid reservoir 324. The sample controller 311 may control access of the cleaning fluid to the inlet path 310. In one example, a sample queue in the inlet path 310 may be separated by a cleaning fluid, such as a detergent, oil, or a combination thereof.

As illustrated, the sequencing device 16 may include one or more cartridges, such as a sample preparation cartridge 320 and a sequencing data acquisition cartridge 322. The sample enters the sample preparation cartridge 320, is prepared according to the specific configuration and reagents available in the cartridge 320, and enters the sequencing data acquisition cartridge 322 to be, for example, plated and imaged during cluster generation in a particular embodiment. In the depicted embodiment, the sample may be applied to the sample slot without being prepared for a particular assay. In other embodiments, the sample preparation may occur being the sample enters the system 300. Further, the sequencing device may not include any sample preparation cartridge 320. However, providing a sample preparation cartridge 320 housed within the sequencing device 16 may allow a particular sample to be separated to undergo multiple assays in parallel.

Figure 10:
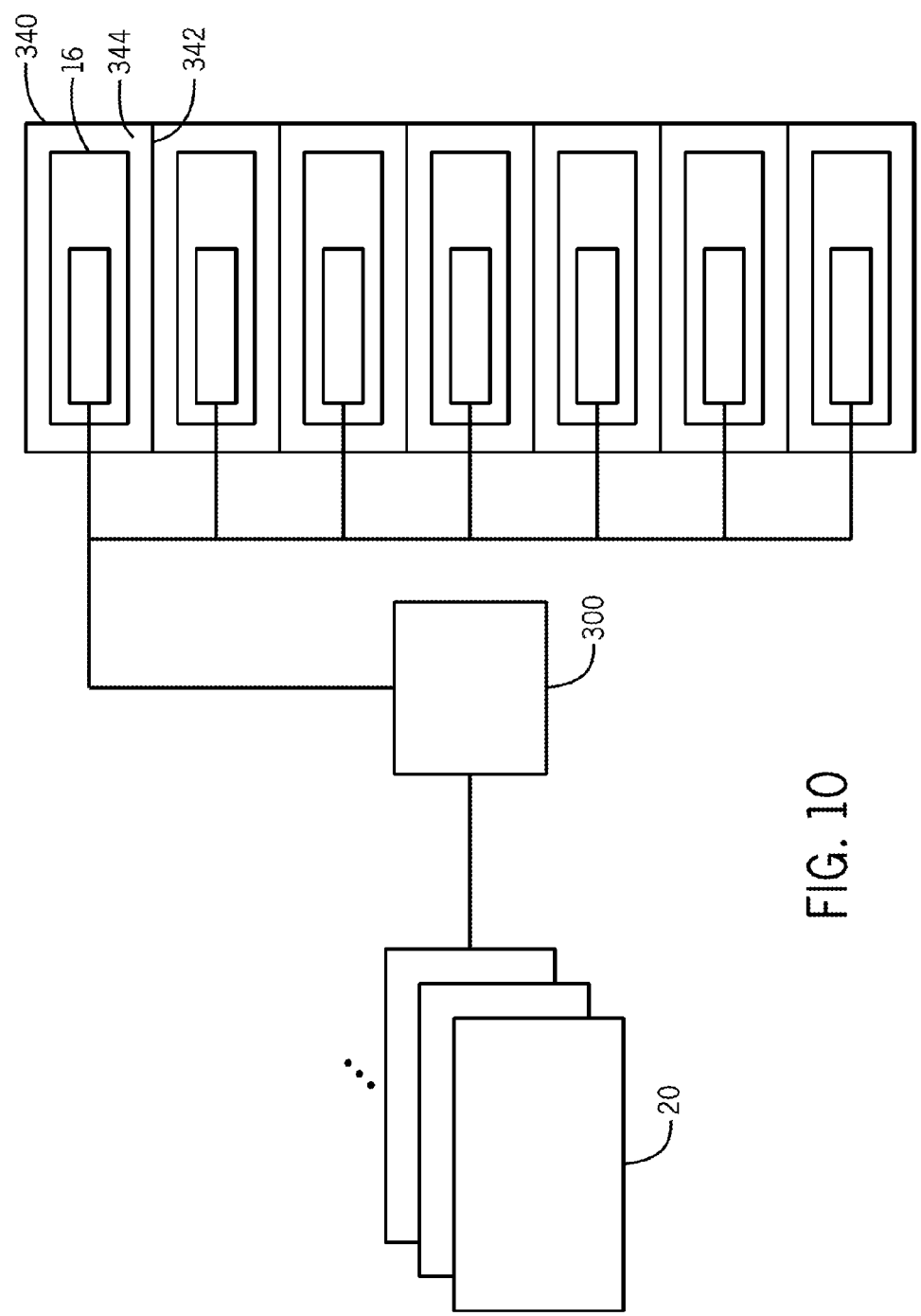
FIG. 10 is a diagrammatical overview of a sample distribution system including a rack-based sequencing system incorporating aspects of the present technique.

For example, the sample distribution system 300 may be used in conjunction with multiple sequencing devices 16 and to apply multiple samples to the devices 20. FIG. 10 is a diagrammatic view of a rack configuration having a cabinet or carriage 340 with a plurality of sequencing devices loaded thereon. The cabinet 340 may include one or more shelves 342 that define one or more reception spaces 344 configured to receive the sequencing devices 16. Although not shown, the sequencing devices 16 may be communicatively coupled to a communication network that permits a user to control operation of the sequencing devices 16. The sequencing devices 16 may also be coupled to the system 10 for sample scheduling.

Figure 11:
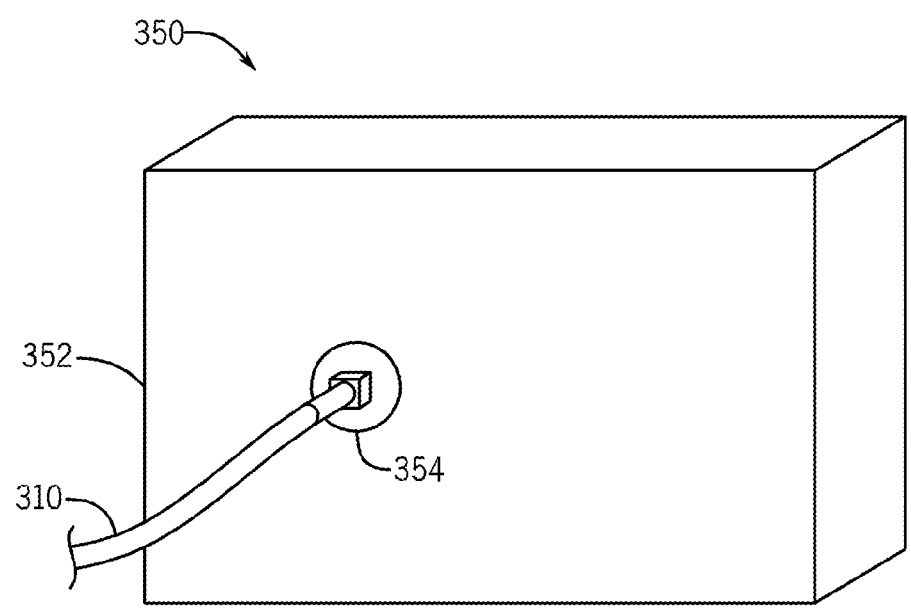
FIG. 11 is a perspective view of a plug-and-play backplane that may be used in conjunction with the system discussed with reference to FIG. 9.

Further, it is envisioned that the sample distribution system 300 may be interoperable with various types of sequencing devices. To that end, the sample distribution system may be implemented as a fluidic backplane that is sized and shaped to plug onto the sample insertion side of the sequencing devices 16. FIG. 11 shows an example of one implementation of backplane 350 that includes a housing 352 and a coupler 354 for the inlet path 310. The coupler 354 is designed to plug into a sample loading port of a sequencing device 16. A sample distribution system 300 may include one or more backplanes 350. In one embodiment, the backplane 350 may be sized and shaped to form a side of a cabinet 340 (see FIG. 10). That is, the backplane 350 may be coupled to the cabinet 340 and the sequencing devices 16 interface with the backplane while positioned in the cabinet 340. The backplane 350 may include one or more electrical connectors and identification features. For example, the backplane 350 may include a USB connector configured to mate to a USB port on the sequencing device 16.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer system for assigning sequencing runs for biological samples, comprising:
    a plurality of sequencing devices respectively configured to acquire sequence data indicative of nucleotide identities from a respective plurality of biological samples during a sequencing run and communicate information related to an availability to sequence at least one of the plurality of biological samples;
    a memory circuit including executable application instructions stored therein; and
    a processor configured to execute the application instructions stored in the memory circuit, wherein the application instructions comprise instructions for:
    receiving information related to the availability of the plurality of sequencing devices;
    receiving identification information for the plurality of biological samples, wherein the identification information comprises sample preparation information for each respective biological sample of the plurality of biological samples;
    identifying a subset of the plurality of sequencing devices that have a sample preparation compatibility with an individual biological sample of the plurality of biological samples based on the sample preparation information;
    assigning the individual biological sample to an individual sequencing device of the subset based at least in part on the information related to the availability and the sample preparation compatibility of each respective sequencing device of the plurality of sequencing devices; and
    providing an indication that the individual sequencing device is available to sequence the individual biological sample based on the information related to the availability and the sample preparation compatibility.

2. The system of claim 1, wherein, when the individual biological sample of the plurality of biological samples has a high priority designation and no sequencing device is available, the application instructions comprise providing an override indication and assigning the individual biological sample to the individual sequencing device based on a determination that a sufficient percentage of sequence data has been acquired of an ongoing incomplete sequencing run.

3. The system of claim 1, wherein, when the individual biological sample of the plurality of biological samples has a high priority designation and no sequencing device is available, the application instructions comprise assigning the individual biological sample to the sequencing device based on a surface sample density of an ongoing sequencing run and providing an indication to add the individual biological sample to the ongoing sequencing run.

4. The system of claim 3, wherein the application instructions comprise providing an indication that the individual biological sample should be tagged to distinguish the biological sample from the ongoing sequencing run.

5. The system of claim 1, wherein the application instructions comprise determining an earliest possible availability for an unavailable sequencing device by determining of a percentage of sufficient completion of an ongoing incomplete sequencing run.

6. The system of claim 1, wherein the application instructions comprise assigning each of the plurality of biological samples to respective sequencing devices based at least in part on an estimated total processing load of the plurality of sequencing devices.

7. The system of claim 6, wherein the assigning comprises smoothing the processing load over a period of time.

8. The system of claim 6, wherein the assigning comprises increasing the processing load at particular times.

9. The system of claim 6, wherein the assigning comprises determining if the sequencing device is capable of performing analysis in the cloud.

10. The system of claim 1, wherein the application instructions comprise instructions for receiving information related to sequencing capabilities of the plurality of sequencing devices, wherein the sequencing capabilities relate to capabilities of operating according to one or more sequencing protocols.

11. The system of claim 10, wherein the instructions for assigning the individual biological sample to the individual sequencing device comprise determining a compatibility between a desired nucleotide sequencing assay type for the individual biological sample and the sequencing capabilities of the individual sequencing device.

12. The system of claim 1, wherein the application instructions comprise providing instructions to a sample loading system to load the individual biological sample into the assigned individual sequencing device when the assigned individual sequencing device is available.

13. The system of claim 1, wherein the memory circuit and the processor are disposed on one of the plurality of sequencing devices.

14. The system of claim 1, wherein the subset comprises sequencing devices of the plurality of sequencing devices from a particular manufacturer.

15. The system of claim 1, wherein the sample preparation information comprises sample tag information, and wherein the subset comprises sequencing devices of the plurality of sequencing devices configured to sequence multiple biological samples simultaneously when at least one of the multiple biological samples comprises the sample tag.

16. The system of claim 1, wherein the individual sequencing device is configured to simultaneously sequence a predetermined number of biological samples prepared according to a same sample preparation protocol subset.

17. The system of claim 1, wherein the individual sequencing device is available when the predetermined number of biological samples has not yet been loaded onto the individual sequencing device.

18. The system of claim 1, wherein the application instructions comprise instructions for identifying the subset of the plurality of sequencing devices further based on a compatibility between sequencing parameter information of the individual biological sample and sequencing capabilities of the plurality of sequencing devices.

19. The system of claim 1, wherein the application instructions comprise instructions for interrupting an ongoing sequencing run of the individual biological sample based on a presence of a homopolymer region of interest in the sequence data.

20. The system of claim 19, wherein the application instructions comprise instructions for reassigning the individual biological sample to another sequencing device of the subset after the interrupting based on the presence of a homopolymer region of interest in the sequence data.

21. The system of claim 1, wherein the application instructions comprise instructions for reassigning the individual biological sample to another sequencing device of the plurality of sequencing devices based on an analysis of the sequence data of other biological samples of the plurality of biological samples.

* * * * *